US011255818B2

(12) United States Patent
Jin et al.

(10) Patent No.: US 11,255,818 B2
(45) Date of Patent: *Feb. 22, 2022

(54) METHOD FOR RELATIVE QUANTITATIVE ANALYSIS OF POLYMER USING MALDI MASS SPECTROMETRY

(71) Applicant: LG Chem, Ltd., Seoul (KR)

(72) Inventors: Kyoungjoo Jin, Daejeon (KR); Yongjin Bae, Daejeon (KR); Young Hee Lim, Daejeon (KR); Yeu Young Youn, Daejeon (KR)

(73) Assignee: LG Chem, Ltd.

( * ) Notice: Subject to any disclaimer, the term of this patent is extended or adjusted under 35 U.S.C. 154(b) by 0 days.

This patent is subject to a terminal disclaimer.

(21) Appl. No.: 16/766,913

(22) PCT Filed: Jul. 12, 2019

(86) PCT No.: PCT/KR2019/008610
§ 371 (c)(1),
(2) Date: May 26, 2020

(87) PCT Pub. No.: WO2020/045821
PCT Pub. Date: Mar. 5, 2020

(65) Prior Publication Data
US 2020/0371065 A1 Nov. 26, 2020

(30) Foreign Application Priority Data

Aug. 30, 2018 (KR) .................. 10-2018-0102447
Apr. 5, 2019 (KR) .................. 10-2019-0040021

(51) Int. Cl.
*G01N 27/64* (2006.01)
*H01J 49/00* (2006.01)
*H01J 49/16* (2006.01)

(52) U.S. Cl.
CPC .......... *G01N 27/64* (2013.01); *H01J 49/0036* (2013.01); *H01J 49/164* (2013.01)

(58) Field of Classification Search
CPC ... G01N 27/64; G01N 33/442; H01J 49/0036; H01J 49/164
(Continued)

(56) References Cited

U.S. PATENT DOCUMENTS 10,991,559 B2 * 4/2021 Bae ................. G01N 33/442
2002/0092366 A1 7/2002 Brock et al.
(Continued)

FOREIGN PATENT DOCUMENTS

EP 1358012 B1 8/2008
JP H05503350 A 6/1993
(Continued)

OTHER PUBLICATIONS

Extended European Search Report including Written Opinion for Application No. EP19855631.8 dated Dec. 21, 2020, 9 pgs.
(Continued)

*Primary Examiner* — Michael Maskell
(74) *Attorney, Agent, or Firm* — Lerner, David, Littenberg, Krumholz & Mentlik, LLP

(57) ABSTRACT

The present invention provides a method for relative quantitative analysis of a polymer using MALDI mass spectrometry, the method comprising the steps of: (S1) electrospraying a solution containing a polymer sample and a matrix through a mask to prepare a plurality of polymer specimens with a thickness variation of 30% or less according to the concentration of the polymer sample; (S2) irradiating the respective plurality of polymer specimens with laser to obtain MALDI mass spectra; and (S3) creating a
(Continued)

quantitative calibration curve from peak results of the MALDI mass spectra by using a signal of the polymer sample.

19 Claims, 10 Drawing Sheets

(58) Field of Classification Search
 USPC .......................................... 250/281, 282, 288
 See application file for complete search history.

(56) References Cited

U.S. PATENT DOCUMENTS

| | | | |
|---|---|---|---|
| 2004/0119010 | A1 | 6/2004 | Perryman et al. |
| 2004/0217276 | A1 | 11/2004 | DiCesare |
| 2006/0138319 | A1 | 6/2006 | Barnes et al. |
| 2010/0065740 | A1 | 3/2010 | Iwamoto et al. |
| 2012/0058009 | A1 | 3/2012 | Nogami et al. |
| 2016/0148793 | A1* | 5/2016 | Kim ................... H01J 49/164 250/282 |
| 2016/0172174 | A1 | 6/2016 | Takahashi |
| 2017/0242030 | A1 | 8/2017 | Novak et al. |
| 2018/0172700 | A1 | 6/2018 | Novak et al. |

FOREIGN PATENT DOCUMENTS

| | | | |
|---|---|---|---|
| JP | 2004529325 | A | 9/2004 |
| JP | 2006504971 | A | 2/2006 |
| JP | 2006226717 | A | 8/2006 |
| JP | 2006525525 | A | 11/2006 |
| JP | 2007263896 | A | 10/2007 |
| JP | 2012032279 | A | 2/2012 |
| JP | 2012230801 | A | 11/2012 |
| JP | 2016114400 | A | 6/2016 |
| KR | 101434092 | B1 | 8/2014 |
| KR | 20170013073 | A | 2/2017 |
| KR | 20170013362 | A | 2/2017 |
| KR | 20190040652 | A | 4/2019 |
| KR | 20190059496 | A | 5/2019 |
| WO | 03040715 | A1 | 5/2003 |
| WO | 2008129850 | A1 | 10/2008 |
| WO | 2010100816 | A1 | 9/2010 |

OTHER PUBLICATIONS

International Search Report for Application No. PCT/KR2019/008610 dated Oct. 15, 2019, 2 pages.
Schwarzinger, et al., "Quantitative Analysis of Polymer Additives with MALDI-TOF MS Using an Internal Standard Approach," J. Am.Soc. Mass Spectrom., Mar. 27, 2002, pp. 1120-1125, vol. 23.
Axelsson, J. et al., "Improved Reproducibility and Increased Signal Intensity in Matrix-assisted Laser Desorption/Ionization as a Result of Electrospray Sample Preparation", Rapid Communications in Mass Spectrometry, Dec. 1998, pp. 209-213, vol. 11.
Jeong, K.H. Et Al., "Focused Electrospray Deposition for Matrix-assisted Laser Desorption/Ionization Mass Spectrometry", Bulletin of the Korean Chemical Society, Aug. 2010, pp. 2293-2298, vol. 31, No. 8.
Li, S. et al., "Electrospray deposition device used to precisely control the matrix crystal to improve the performance of MALDI MSI", Scientific Reports, Nov. 2016, pp. 1-10, vol. 6, Article No. 37903.

* cited by examiner

[Fig. 1]
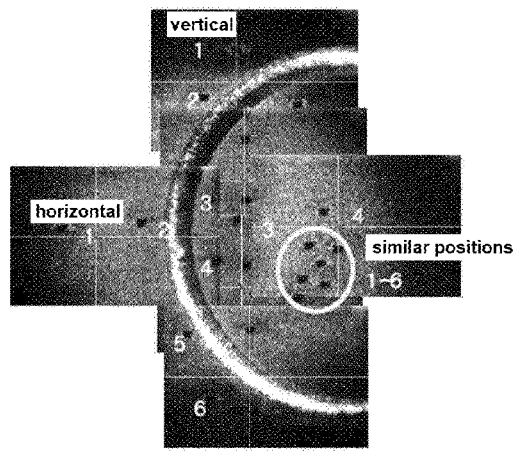
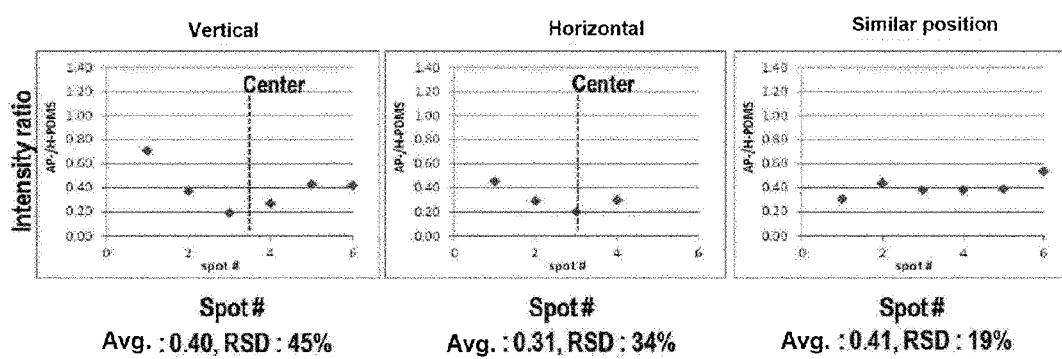
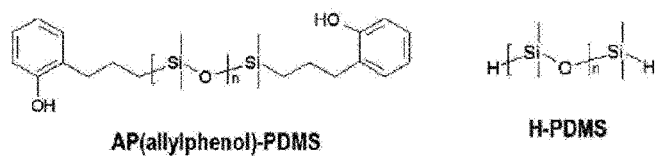

[Fig. 2]
1) BHB-PPG + PPG sample
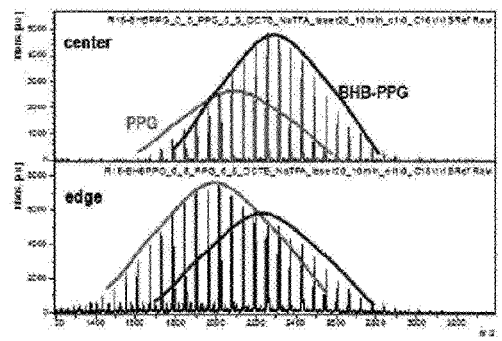
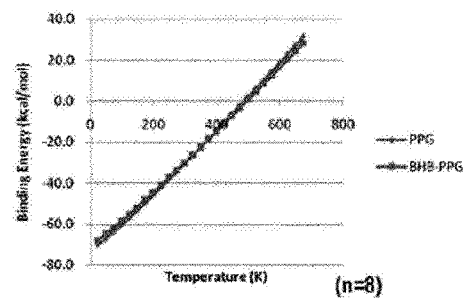
2) AP-PDMS + H-PDMS sample
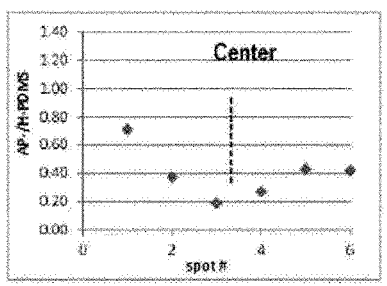
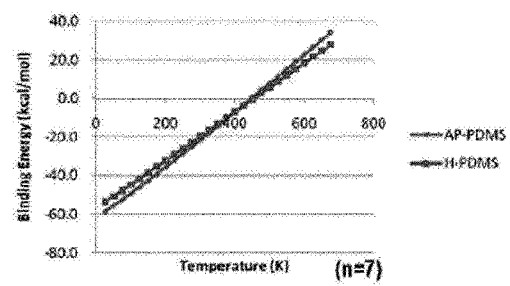
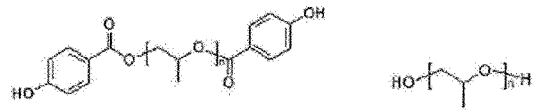
BHB-PPG          PPG
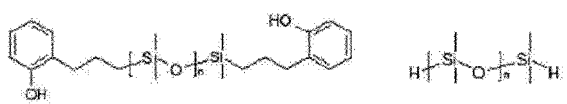
AP(Allylphenol)-PDMS    H-PDMS

[Fig. 3]
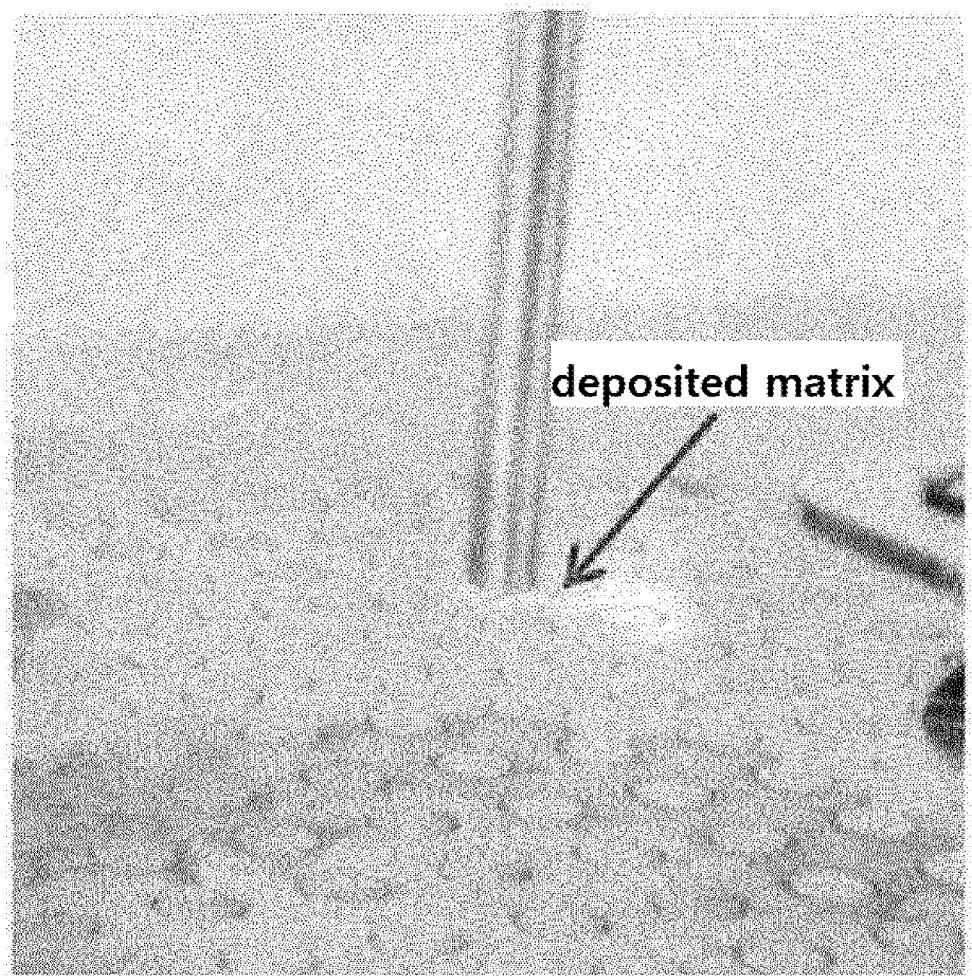

[Fig. 4a]
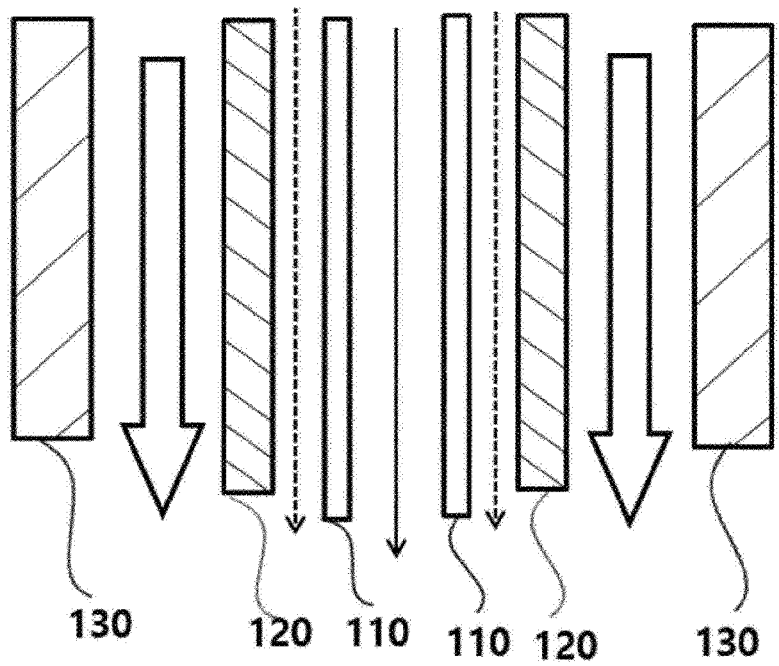
130　120 110　110 120　130
[Fig. 4b]
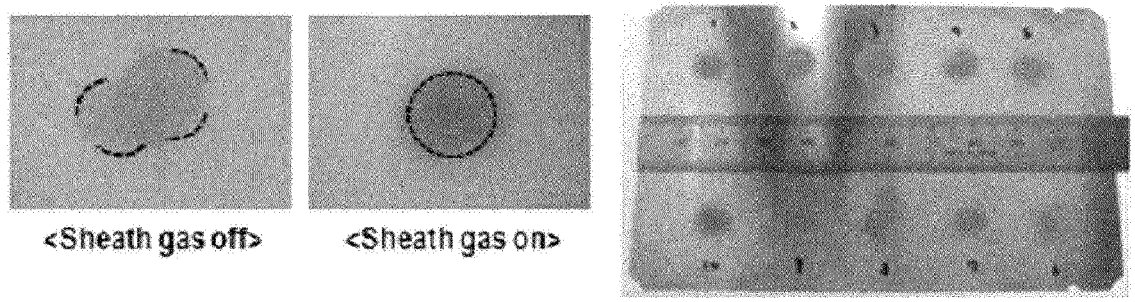
<Sheath gas off>　　<Sheath gas on>

[Fig. 4c]
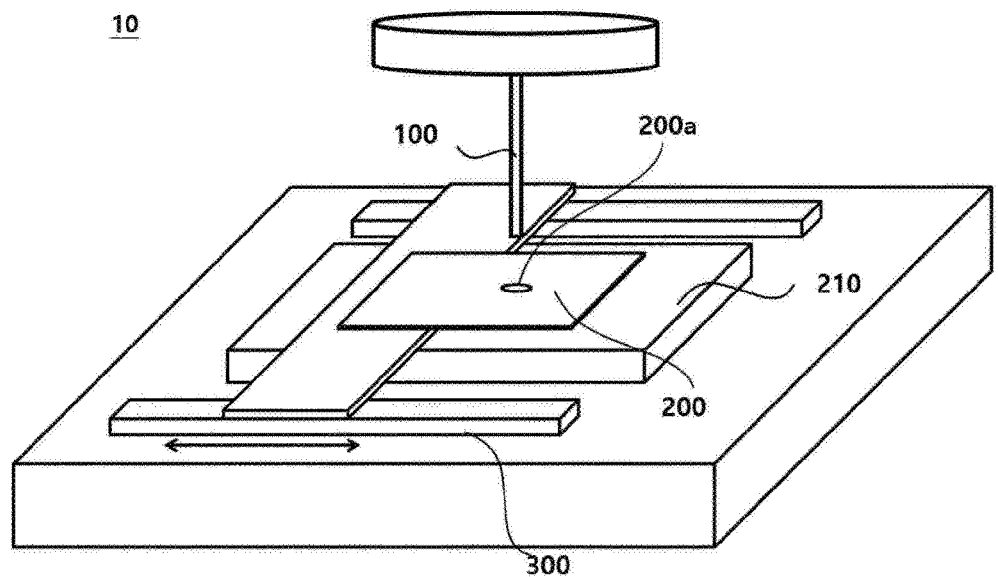
[Fig. 4d]
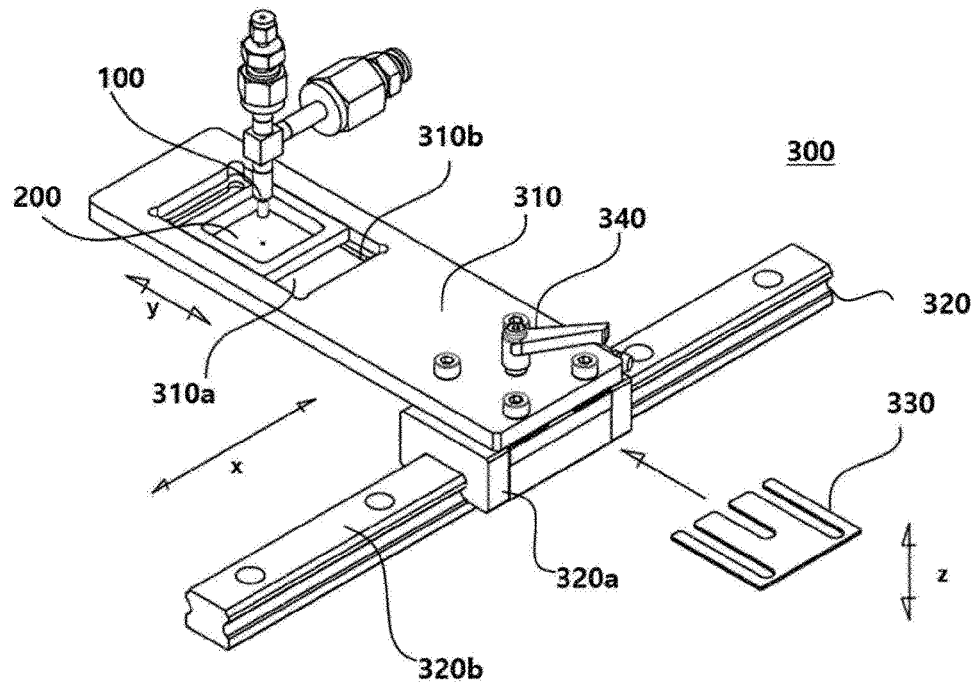

[Fig. 5]
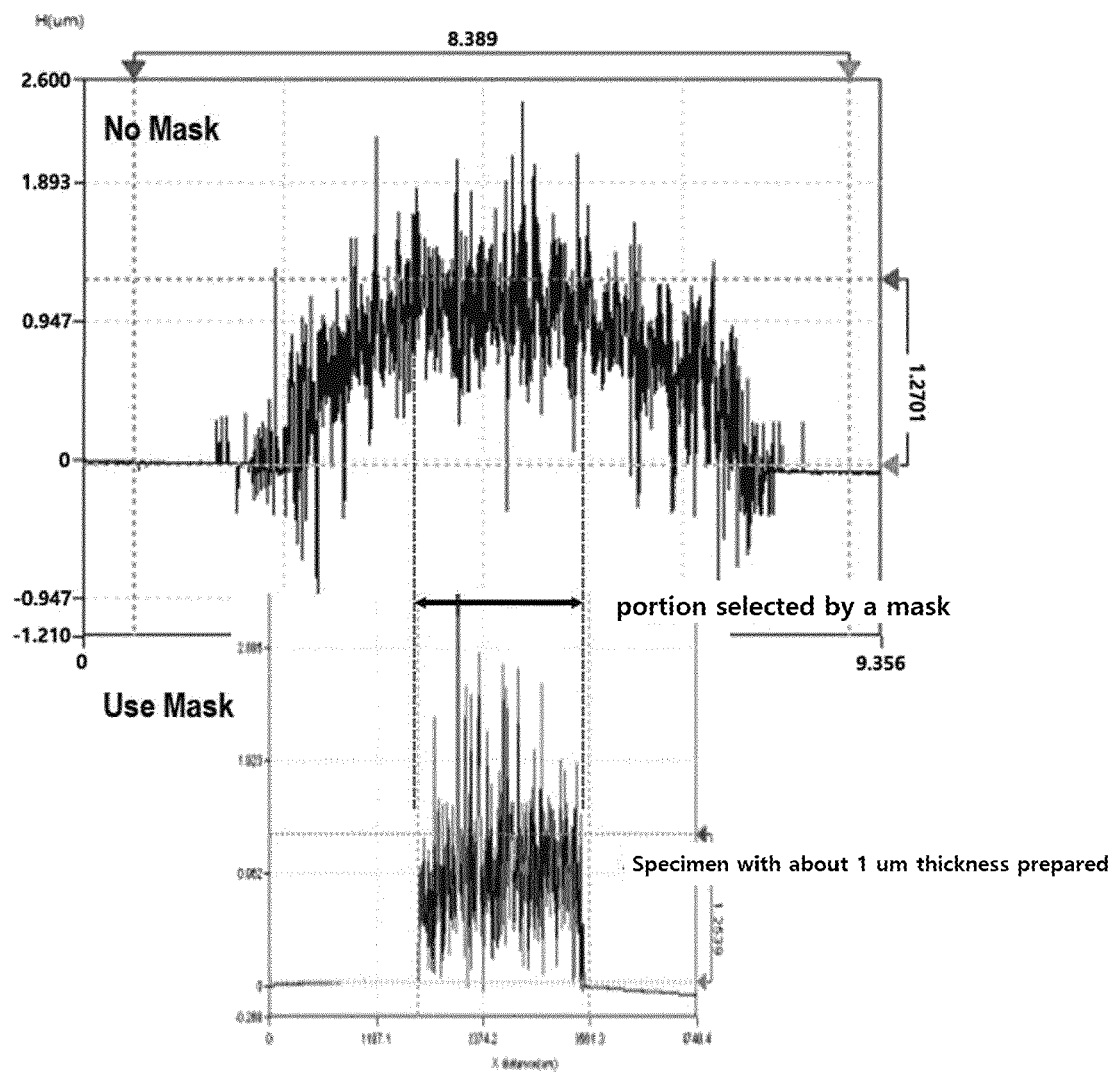
[Fig. 6]
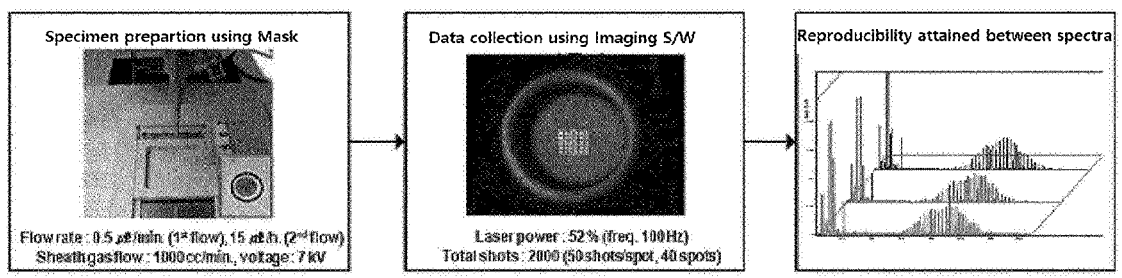

[Fig. 7]
A.
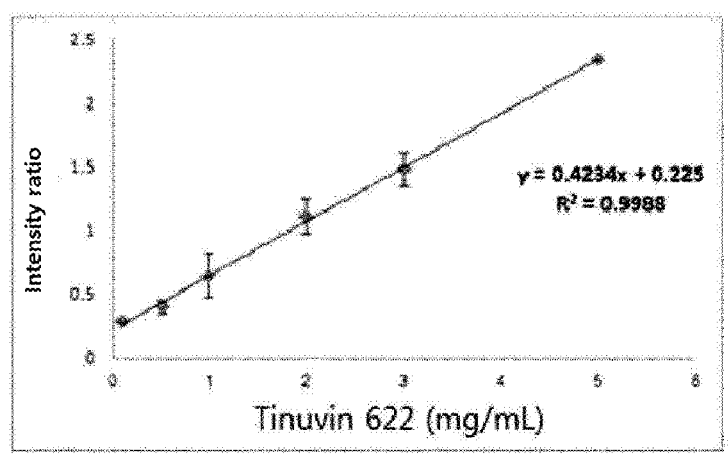
B.
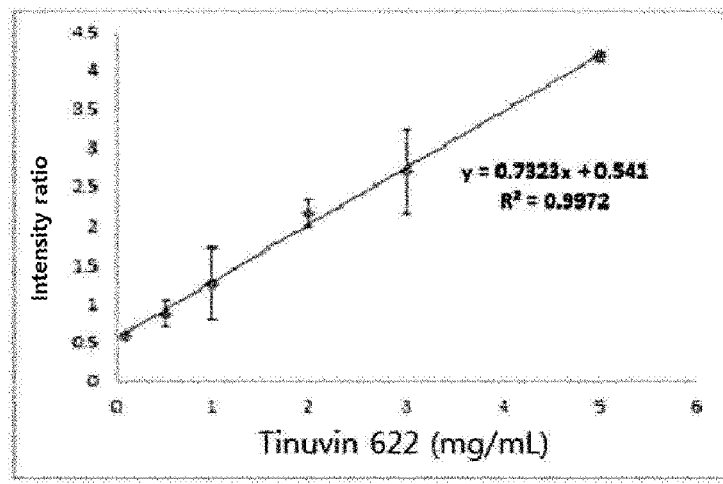

[Fig. 8a]
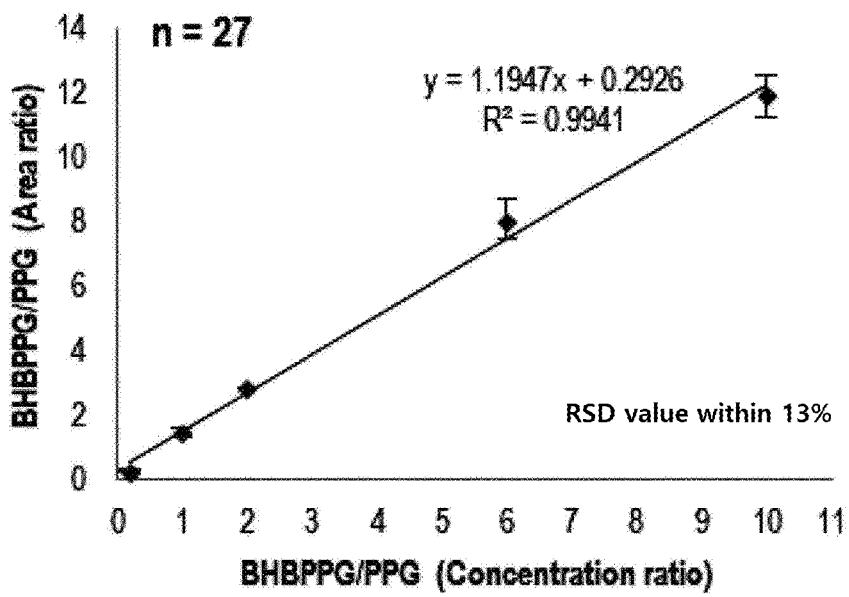
[Fig. 8b]
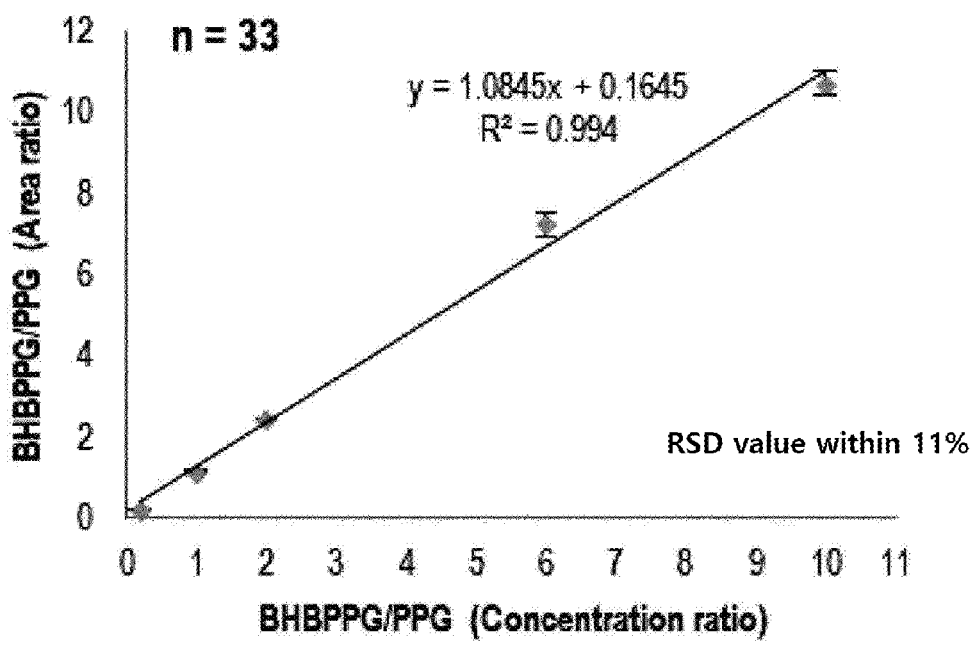

[Fig. 8c]
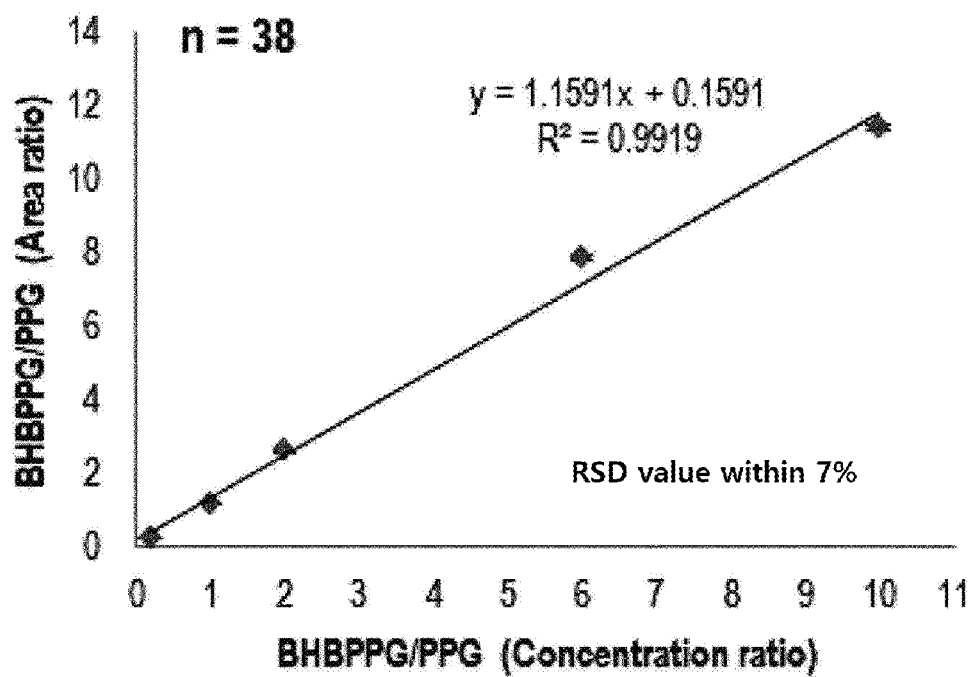

[Fig. 9]
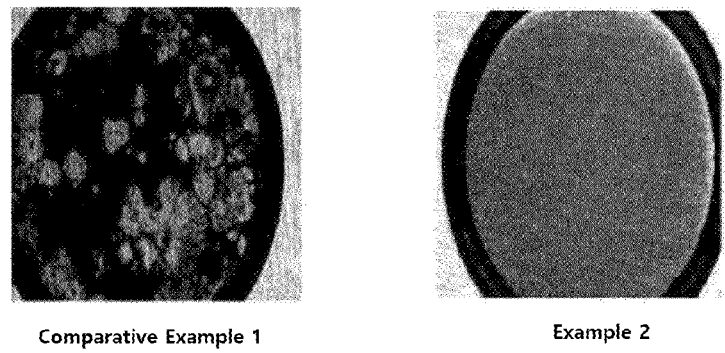
Comparative Example 1          Example 2
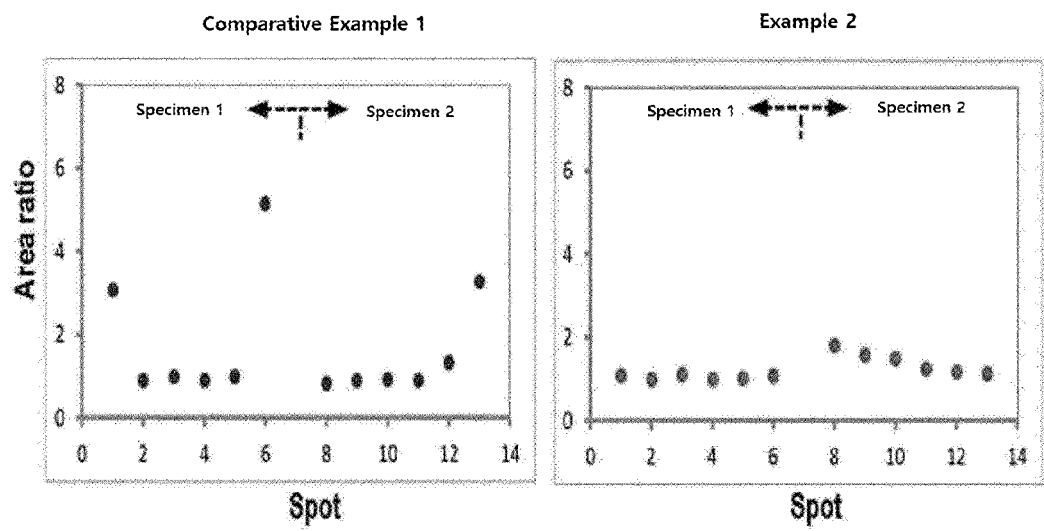

000
METHOD FOR RELATIVE QUANTITATIVE ANALYSIS OF POLYMER USING MALDI MASS SPECTROMETRY

CROSS-REFERENCE TO RELATED APPLICATIONS

This application is a national phase entry under 35 U.S.C. § 371 of International Application No. PCT/KR2019/008610 filed Jul. 12, 2019, which claims priority from Korean Patent Application No. 10-2018-0102447 filed Aug. 30, 2018 and Korean Patent Application No. 10-2019-0040021 filed Apr. 5, 2019, all of which are incorporated herein by reference.

BACKGROUND OF THE INVENTION

1. Field of the Invention

The present invention relates to a method of relative quantitative analysis of a polymer using MALDI mass spectrometry, and more particularly, to a method of performing relative quantitative analysis by obtaining a MALDI spectrum for a polymer sample with a uniform thickness and preparing a quantitative calibration curve using the peak signal.

2. Description of the Related Art

Matrix-assisted laser desorption ionization (MALDI) is a technique that indirectly ionizes a specimen through a matrix, and is easy to use for mass spectrometry but difficult to use for quantitative analysis of polymer materials due to lack of spectrum reproducibility.

Nevertheless, techniques for quantitative analysis of specimens using MALDI mass spectrometry have been developed. For example, it has been reported that if a spectrum is prepared by maintaining the temperature of a plume which is a vapor generated from a specimen by laser pulse in MALDI constant, the reproducibility of the spectrum can be attained and a quantitative calibration curve can be obtained, which allows for quantitative analysis.

Meanwhile, the inventors have found that the thickness of the polymer specimen is a factor influencing the pattern of the MALDI spectrum, and have prepared a specimen having a uniform thickness by uniformly adjusting the thickness of the specimen through the electrospray applied with a mask (Korean Patent Application No. 10-2017-0130010, filed on Oct. 11, 2017, Applicant: LG Chem Co., Ltd.). All contents disclosed in the said patent document are incorporated as a part of this specification.

Furthermore, the present inventors continued to study techniques for efficiently performing quantitative analysis of a polymer using a polymer specimen having a uniform thickness. Thus, the present inventors have found that a linear quantitative calibration curve can be obtained after attaining a reproducible MALDI mass spectrum from the polymer specimen having a uniform thickness by using the peaks of the materials appearing in the spectrum, thereby completing the present invention.

SUMMARY OF THE INVENTION

Accordingly, an object of the present invention is to provide a method for relative quantitative analysis of a polymer comprising preparing polymer specimens having a uniform thickness made from polymer samples having various concentrations to obtain a reproducible MALDI mass spectrum and preparing a quantitative calibration curve by using peaks of the matrix or internal standard with the peak of the polymer sample appearing in the spectrum.

According to one aspect of the present invention, there is provided a method for relative quantitative analysis of a polymer by MALDI mass spectrometry, comprising the steps of:

(S1) preparing a plurality of polymer specimens having a thickness variation of 30% or less by electrospray of a solution containing a polymer sample and a matrix through a mask for each concentration of the polymer sample;

(S2) obtaining a MALDI mass spectrum by irradiating a laser to each of the plurality of polymer specimens; and (S3) preparing a quantitative calibration curve with a signal of a polymer sample from peak results of the MALDI mass spectrum.

The polymer sample may comprise poly-(N-b-hydroxyethyl-2,2,6,6-tetramethyl-4-hydroxypiperidylsuccinate (Tinuvin 622), 2,2-bis(hydroxymethyl)butyric acid-poly(propylene glycol) (BHB-PPG), allylphenol-polydimethylsiloxane (AP-PDMS), H-polydimethylsiloxane (H-PDMS) or mixtures thereof.

The quantitative calibration curve may be prepared by calculating a signal intensity ratio of the polymer sample and the matrix from the peak result of the MALDI mass spectrum and plotting it according to the concentration of the polymer sample.

In the step (S1), the polymer specimen may be prepared by additionally adding an internal standard to the solution containing the polymer sample and the matrix. In this case, the quantitative calibration curve for the polymer specimen having the polymer sample and the matrix additionally added with the internal standard may be prepared by calculating a signal intensity ratio of the polymer sample and the internal standard from the MALDI mass spectrum obtained for the polymer specimen, and plotting it according to the concentration ratio of the polymer sample and the internal standard.

The internal standard may be a polymer compound selected from poly(ethylene glycol) (PEG), poly(propylene glycol) (PPG), polystyrene (PS), and mixtures of two or more thereof.

The preparing the polymer specimen by electrospray through the mask comprises the steps of (i) preparing an electrospray apparatus comprising a sample plate and an electrospray main nozzle and mounting a mask on the sample plate; and (ii) electrospraying a solution containing a polymer sample and a matrix onto the mask-mounted sample plate by the main nozzle, wherein the mask may comprise a hole through which the polymer sample solution electrosprayed from the main nozzle may pass onto the sample plate so as to obtain a polymer specimen having a small thickness variation on the sample plate.

In the step (ii), the electrospray may be performed after additionally adding an internal standard to the solution containing the polymer sample and the matrix.

The diameter of the hole included in the mask may be 1 to 2 mm. In addition, the mask may be made of stainless steel or aluminum.

The mounting of the mask on the sample plate may further comprise the step of adjusting the position of the mask in the direction of at least one of the x-axis, the y-axis and the z-axis.

The electrospray apparatus may further comprise an auxiliary nozzle surrounding the main nozzle and coaxial with the main nozzle, and the electrospray of the polymer sample solution onto the sample plate by the main nozzle may further comprise the step of spraying a solvent by the auxiliary nozzle to prevent the matrix from being deposited around the main nozzle.

In addition, the electrospray apparatus may further comprise a sheath gas supply pipe surrounding the auxiliary nozzle and coaxial with the auxiliary nozzle, and the electrospray of the polymer sample solution onto the sample plate by the main nozzle may further comprise the step of spraying a sheath gas from the sheath gas supply pipe to guide the solution so that the solution is sprayed to a predetermined position of the sample plate.

The area where the polymer sample solution is electrosprayed on the sample plate may be 40 to 180 mm$^2$, specifically 40 to 80 mm$^2$.

The polymer specimen may have a thickness in the range of 500 nm to 10 µm.

The thickness variation of the polymer specimen may be 30% or less as measured at three or more spots on the same specimen (spot-to-spot).

The relative standard deviation (RSD) range, which indicates the error of the result of the MALDI mass spectrum measured on the polymer specimen, may be ±15% or less as measured at three or more spots on the same specimen (spot-to-spot).

Effect of the Invention

According to the present invention, a uniform polymer specimen having a thickness variation of 30% or less is prepared by electrospray with a mask to obtain a reproducible MALDI mass spectrum and a quantitative calibration curve is prepared using a peak of a matrix or internal standard, thereby allowing for relative quantitative analysis of polymer samples having various concentrations.

BRIEF DESCRIPTION OF THE DRAWINGS

FIG. 1 shows the difference in MALDI mass spectrum depending on the analysis position of the specimen for the specimen prepared from the prior art.

FIG. 2 shows the difference in MALDI mass spectrum depending on the thickness of the specimen and the difference in ionization efficiency depending on the temperature of the plume.

FIG. 3 shows a phenomenon that the matrix is deposited at the tip of the nozzle in the spraying process using the electrospray of the prior art.

FIGS. 4a to 4d schematically illustrate an electrospray apparatus with a mask for manufacturing a polymer specimen according to one embodiment of the present invention and an application process thereof.

FIG. 5 illustrates a process of manufacturing a specimen having a thickness of 1 µm by selecting a center of the specimen from a wide area sprayed using a mask according to one embodiment of the present invention.

FIG. 6 shows a data acquisition process from MALDI mass spectrum obtained for the specimen manufactured according to one embodiment of the invention.

FIG. 7 shows a quantitative calibration curve prepared by plotting the signal intensity ratio of the polymer sample and the matrix according to the concentration of the polymer sample, from the results of the MALDI mass spectrum obtained for the polymer specimen manufactured according to Example 1.

FIGS. 8a to 8c are quantitative calibration curves prepared by plotting the signal intensity ratio of the polymer sample and the internal standard according to the concentration ratio of the polymer sample and the internal standard, from the results of the MALDI mass spectrum obtained for the polymer sample prepared according to Example 2 (wherein n represents the repeating unit of the monomer).

FIG. 9 is a result showing the reproducibility evaluation of the MALDI mass spectrum for the specimen manufactured by electrospray through the mask according to Example 2, and the specimen manufactured by the natural drying method according to Comparative Example 1.

DETAILED DESCRIPTION OF THE INVENTION

Since various modifications and variations can be made in the present invention, particular embodiments are illustrated in the drawings and will be described in detail in the detailed description. It should be understood, however, that the invention is not intended to be limited to the particular embodiments, but includes all modifications, equivalents, and alternatives falling within the spirit and scope of the invention.

One embodiment of the invention relates to a method of relative quantitative analysis of a polymer using MALDI mass spectrometry, the method comprising the steps of preparing a polymer specimen (S1); obtaining a MALDI mass spectrum for the polymer specimen (S2); and preparing a quantitative calibration curve with a signal of a polymer sample from peak results of the MALDI mass spectrum (S3).

Hereinafter, specific steps of the method will be described in detail with reference to the accompanying drawings.

<Preparation of Polymer Specimen>

In the present invention, to prepare a polymer specimen for performing MALDI mass spectrometry, a solution containing a polymer sample and a matrix is electrosprayed through a mask. At this time, the polymer specimen is prepared in plural with polymer samples having various concentrations, wherein the concentration of the matrix in each polymer specimen is constant.

In one embodiment of the invention, the polymer sample may be a polymer compound having a molecular weight of 1000 Da or more, such as 3000 to 4000 Da. In addition, the polymer sample has polydispersity. In the present specification, the polymer compound is a mixture of different molecular species having the same repeating unit but not the same molecular weight and the like, and such properties representing various molecular weight distributions are defined as polydipersity. In addition, the polymer samples have the same polydispersity means that the molecular weight distribution pattern is the same for two or more types of polymer samples which have polydispersity.

The polymer sample in the present invention may comprise poly-(N-b-hydroxyethyl-2,2,6,6-tetramethyl-4-hydroxypiperidylsuccinate (Tinuvin 622), 2,2-bis(hydroxymethyl)butyric acid-poly(propylene glycol) (BHB-PPG), allylphenol-polydimethylsiloxane (AP-PDMS), H-polydimethylsiloxane (H-PDMS) or mixtures thereof.

The matrix used in preparing the polymer specimen refers to a material that absorbs energy from an energy source such as a laser and transfers the energy to the polymer sample to be analyzed, thereby heating and ionizing the polymer sample.

The matrix is not particularly limited as long as it can detect a polymer sample, for example, DCTB (trans-2-[3-(4-tert-butylphenyl)-2-methyl-2-propenylidene]malononitrile), DHB (2,5-dihydroxybenzoic acid), CHCA (α-cyanohydroxycinnamic acid), SA (sinapic acid, 3,5-dimethoxy-4-hydroxycinnamic acid) and the like can be used.

In addition, a polymer specimen may be prepared by additionally adding an internal standard to the solution including the polymer sample and the matrix.

The internal standard is used for relatively quantitative analysis of polymer sample. Here, "relative quantification" refers to quantifying the sample by adding a specific internal standard together with a polymer sample to prepare a polymer specimen, and measuring the relative value of the peak result of each sample to the peak result of the internal standard in the MALDI mass spectra of the specimens.

The internal standard may be a polymer compound selected from poly(ethylene glycol) (PEG), poly(propylene glycol) (PPG), polystyrene (PS) and a mixture of two or more thereof. In addition, a polymer having the same main chain as the polymer sample but having a different terminal may be used as the internal standard.

The polymer sample, the matrix and the internal standard may be used in the form of a solution dissolved in an organic solvent such as tetrahydrofuran (THF), xylene or chloroform, respectively, and the concentration thereof may be appropriately selected. For example, the polymer sample may be used at each concentration within the range of 0.1 to 10 mg/ml in the specimen to be prepared. In addition, the matrix and the internal standard may be used at a constant concentration of 0.1 mg/ml and 10 mg/ml, respectively, in each specimen, but are not particularly limited thereto.

The solution containing the polymer sample and the matrix, and optionally the internal standard as described above may be applied to a sample plate, for example, a stainless steel plate, to prepare a polymer specimen for MALDI mass spectrometry.

Meanwhile, the signal ratio of the sample to the matrix or to the internal standard in the MALDI mass spectrum depends on the temperature during the ion generation reaction by laser irradiation. Therefore, it is necessary to control the temperature of the ion generation reaction constantly. If the polymer specimen to be produced has a non-uniform thickness, the temperature may be not uniform when irradiating a laser to the specimen to cause the ion generation reaction, making it difficult to obtain a reproducible MALDI mass spectrum.

For example, FIG. 1 shows the difference in MALDI mass spectrum depending on the analysis position of the specimen for the specimen manufactured from the prior art. It can be found that from the results of MALDI spectra obtained from different positions the spectrum obtained from center of the specimen are different from the spectrum obtained from edge of the specimen. In other words, the spectra changes with tendency from center to edge of the specimen, and the spectra measured at similar positions show a relatively similar tendency.

In MALDI, the spectra tend to coincide with each other when the temperature of the plume which is the vapor generated from the specimen by the laser pulses is the same, but the spectra tend to be different when the temperature of the plume is different. Thus, the result of FIG. 1 means that the temperature of the plume varies depending on the position in the specimen.

In addition, the temperature of the plume is involved in the thickness of the specimen. As the thickness increases, the temperature of the plume tends to increase. Thus, from this general fact, it can be predicted that a factor affecting the MALDI spectrum pattern of polymer is the thickness of the specimen.

FIG. 2 is a result showing the effect of the temperature change according to the thickness of the specimen on the ionization efficiency of the polymer. From the change in intensity of the spectrum according to the specimen position of the BHB-PPG+PPG sample in FIG. 2-1), it can be seen that the signal intensity ratio of the BHB-PPG to PPG is greater in the center than at the edge of the specimen. The cause of this can be predicted from the graph showing a change in Na+ binding energy according to the temperature. FIG. 2 is a graph illustrating a change in Na+ binding energy depending on the temperature. The lower the Na+ binding energy is, the higher the Na+ affinity is. Therefore, it can be predicted that the higher the temperature, the more ions generated by the BHB-PPG than the PPG. In the case of AP-PDMS+H-PDMS sample of FIG. 2-2), the experimental results can be sufficiently predicted by using the graph of Na+ binding energy according to the temperature.

As such, the temperature of the plume affects the ionization efficiency, and fluctuations in the temperature of the plume may result from differences in the specimen thickness, so that the specimen having a uniform thickness should be used in order to obtain a reproducible MALDI spectral result.

Therefore, the present invention uses an electrospray method using a mask to control the polymer specimen to have a small thickness variation at a plurality of spots in the manufacture of the polymer specimen, and specifically comprises the following steps:

(i) preparing an electrospray apparatus comprising a sample plate and an electrospray main nozzle and mounting a mask on the sample plate; and (ii) electrospraying a solution containing a polymer sample and a matrix (hereinafter referred to as "polymer sample solution" or "sample solution") onto the mask-mounted sample plate by the main nozzle.

In addition, according to an embodiment of the present invention, the electrospray may be performed by additionally adding an internal standard to the solution containing the polymer sample and the matrix in the step (ii).

The mask may comprise a hole through which the polymer sample solution electrosprayed from the main nozzle may pass onto the sample plate so as to obtain a polymer specimen having a small thickness variation on the sample plate.

The material of the mask is not particularly limited, but may be stainless steel or aluminum. In addition, the shape of the mask may also vary, including a rectangle, a circle, and the like, and the length of one side of the mask may be several cm in size. For example, when the mask has a rectangular shape, the length of one side may be 1 to 4 cm, and when the mask has a circular shape, the diameter may be 1 to 4 cm. In this case, the holes provided in the mask may have a size of, for example, 1 to 2 mm in diameter.

Electrospray through this mask is performed to spread the sample solution around the hole of the mask. For example, the diameter of jetting hole for the sample solution may be 4 to 15 mm and the area in which the sample solution is sprayed may be in the range of 40 to 180 $mm^2$, specifically 40 to 80 $mm^2$. That is, the jetting area of the sample solution for electrospray according to the present invention is not limited to the size of the mask hole, but spraying may be carried out widely including the vicinity of the mask hole.

In this manner, the polymer sample solution passing through the hole may be applied on the sample plate with a uniform and thin thickness, and the solution not passing through the hole remains on the mask. If the jetting area is limited to the size of the mask hole, it may be difficult to produce a specimen of uniform thickness.

In one embodiment of the present invention, the thickness of the polymer specimen manufactured by the spraying as described above may be 500 nm to 10 μm, such as 0.5 to 5 μm or 1 to 2 μm. When satisfying such a thickness range, it is possible to maintain uniformity to minimize the thickness variation while ensuring a thickness capable of analyzing the polymer sample.

As such, the uniform polymer specimen may be manufactured by selecting only a portion having a small thickness variation from regions where the sample solution is sprayed onto the sample plate.

The electrospray method generally has application to various fields from the viewpoint that the polymer sample can be sprayed and deposited more uniformly over a large area. Electrospray is easy to build a system because of the simple shape and structure of the nozzle, and very simple to produce droplets from hundreds of nanometers to tens of microns. In addition, since the droplets have a monodisperse distribution and the surface of the droplets are charged as well, there is the advantage that the droplets are hardly to bind to each other and thus easy to be controlled. In addition, it is possible to spray in a large area and to spray at atmospheric pressure. Also, it is possible to produce a specimen having more stable characteristics due to electrostatic effect.

However, when spraying a solution containing a polymer sample and a matrix and, optionally, an additional internal standard in a spraying process using a general electrospray, a phenomenon may occur in which the matrix is deposited at the tip of the nozzle (see FIG. 3). Due to the matrix deposited at the tip of the nozzle, there was a problem that the reproducibility of the electrospray of the sample was inferior. In other words, due to the matrix deposited at the tip of the nozzle, it was difficult for the sample to be sprayed to a certain position.

This problem may be overcome by using an auxiliary nozzle together with the main nozzle. For example, as can be seen in the electrospray apparatus used in the embodiment of the present invention of FIGS. 4a to 4d and its application process, the nozzle portion 100 of the electrospray apparatus may comprise a main nozzle 110 for jetting a solution containing a polymer sample and a matrix, and optionally an additional internal standard, and an auxiliary nozzle 120 surrounding the main nozzle 110 and coaxial with the main nozzle 110, wherein the auxiliary nozzle 120 is adapted to spray a solvent (see FIG. 4a). In FIG. 4a, a solid line arrow in the main nozzle 110 indicates a flow of a polymer sample sprayed from the main nozzle 110, and a dotted line arrow in the auxiliary nozzle 120 indicates a flow of a solvent sprayed from the auxiliary nozzle 120. That is, by additionally spraying the solvent from the auxiliary nozzle 120 surrounding the main nozzle 110 while spraying the polymer sample solution from the main nozzle 110, it is possible to prevent the phenomenon of the deposition of the matrix at the tip of the nozzle, which is a problem in the spraying process using the electrospray according to the prior art, thereby improving the reproducibility of electrospray of the polymer sample. Tetrahydrofuran (THF) may be used as the solvent to be sprayed through the auxiliary nozzle.

In addition, the polymer sample solution electrosprayed from the main nozzle 110 is to be sprayed to a predetermined position. The inlet of the main nozzle 110 may protrude further toward the sample plate than the inlet of the auxiliary nozzle 120. For example, the inlet of the main nozzle 110 may protrude about 1 mm to 2 mm toward the sample plate than the inlet of the auxiliary nozzle 120. The amount of solvent to be sprayed from the auxiliary nozzle 120 may be, for example, 30 to 60% of the amount of solvent sprayed from the main nozzle 110.

Additionally or alternatively, by providing a sheath gas supply pipe 130 surrounding the auxiliary nozzle 120 and coaxial with the auxiliary nozzle 120, a sheath gas is also sprayed to around the polymer sample when the polymer sample is sprayed from the main nozzle 110, so that the sheath gas guides the polymer sample to be sprayed to a predetermined position. In FIG. 4a, the thick arrow in the sheath gas supply pipe 130 indicates the sheath gas sprayed from the sheath gas supply pipe 130. Thereby, the reproducibility of the electrospray of a polymer sample can be improved. As the sheath gas, for example, nitrogen gas ($N_2$) may be used. For example, nitrogen gas may be released at 100 to 1000 cc/min, and in one embodiment 1000 cc/min.

As described above, in the present invention, the solvent is sprayed from the auxiliary nozzle 120 surrounding the main nozzle 110 or the sheath gas is sprayed from the sheath gas supply pipe 130 surrounding the auxiliary nozzle 120 and coaxial with the auxiliary nozzle 120 to around the sample solution to be sprayed, while spraying the sample solution from the main nozzle 110. Accordingly, the sample solution electrosprayed from the main nozzle 110 can be sprayed to a predetermined position on the sample plate.

FIG. 4*b* shows that the sample solution is loaded at a predetermined position when the sheath gas is used. For example, reproducibility was confirmed by repeating electrospray 10 times at 2 cm intervals.

In addition, referring to FIG. 4*c*, in one embodiment of the present invention, the mask position adjusting unit 300 may be used together with the mask 200 in the manufacture of the polymer specimen. That is, when the polymer sample solution is electrosprayed on the sample plate placed on the sample stage 210, the mask 200 is placed on the sample plate for electrospray so that only a portion having a small variation in thickness can be selected as a specimen from the regions where the polymer sample is sprayed on the sample plate placed on the sample stage 210. In addition, since the mask 200 is mounted in the mask position adjusting unit 300, the position of the mask 200 on the sample plate may be adjusted by the mask position adjusting unit 300.

The center of the mask 200 includes a hole 200*a* that generally corresponds to the size of the specimen corresponding to the portion having the desired thickness variation. Samples that do not pass through the hole 200*a* among the samples to be electrosprayed remain on the mask 200. When the mask 200 according to FIG. 4*c* is mounted on the sample plate with the improved reproducibility of the electrospray of the polymer sample as described with reference to FIG. 4*a*, the polymer sample to be electrosprayed may pass through the hole 200*a* of the mask 200 and be placed on the sample plate to produce a specimen having a desired thickness variation.

FIG. 5 illustrates a process of manufacturing a specimen having a thickness of 1 μm by selecting a center of the specimen from a widely sprayed area using a mask according to an exemplary embodiment of the present invention. Through this process, a sample having a thickness variation of 30% or less, for example 25%, finally remains on the sample stage 210.

As described above, the mask 200 may be made of stainless steel, aluminum, or the like and may have a rectangular or circular shape, and in addition various materials and shapes are possible. For example, when the mask 200 has a rectangular shape, the length of one side may be 1 to 4 cm, and when the mask 200 has a circular shape, the diameter may be 1 to 4 cm. In this case, the diameter of hole 200*a* may be, for example, 1 to 2 mm.

In addition, referring to FIG. 4*d*, the mask position adjusting unit 300 may comprise a mask holder 310 on which the mask 200 can be mounted.

In one embodiment of the present invention, the mask holder 310 may further comprise an opening 310*a*, in which the mask 200 may be mounted and the mounted mask 200 may move on one axis direction (e.g., y-axis). The opening 310*a* may have, for example, a rectangular shape and the width of one side of the rectangle of the opening 310*a* may match the width of the mask 200. The width of the other side of the opening 310*a* is larger than the width of the mask 200 so that the mask 200 mounted in the opening 310*a* can be moved and mounted. Both edges of the opening 310*a* may include a convex portion 310*b*, and thus the mask 200 may be placed on the convex portion 310*b* of the opening 310*a*.

The mask position adjusting unit 300 comprises a linear motion rail 320 extending perpendicular to the length direction of the mask holder 310, and the mask holder 310 may be mounted to a mounting portion 320*a* of the linear motion rail 320. The mask holder 310 is fixed to the mounting portion 320*a* by, for example, a bolt, and can move on the x-axis on the rail portion 320*b* of the linear motion rail 320. The rail portion 320*b* may further comprise a ruler (see FIG. 4*d*) to display how much the mask holder 310, that is, the mask 300 which is mounted on the mask holder 310 moves on the x-axis.

If the mask holder 310 moves in the x-axis direction on the linear motion rail 320, the mask 300 may move in the y-axis direction within the opening 310*a* of the mask holder 310, as described above. In addition, the mask position adjusting unit 300 may adjust the height of the mask holder 310 in the z-axis direction (the direction perpendicular to the upper surface of the sample stage 210). As the plate on which the specimen is placed, various plates such as a stainless steel plate and an ITO glass may be used. Therefore, the height (the height in the z-axis) of the mask holder 310, i.e., the height of the mask 300 which is mounted on the mask holder 310 needs to be adjusted according to the height of the plate. When the mask holder 310 is mounted on the mounting portion 320*a* of the linear motion rail 320, a spacer 330 for adjusting the height of the mask holder 310 may be disposed between the mask holder 310 and the mounting portion 320*a*. For example, a plurality of spacer may be provided and the number of spacers may be increased from 0 (zero) until the corresponding height is reached. Alternatively, each spacer having a height corresponding to the plate may be provided. The present invention is not limited to the above, and various modifications and changes are possible.

In addition, in one embodiment of the present invention, the mask position adjusting unit 300 may further comprise a fixing unit 340 for fixing the mask holder 310 to the linear motion rail 320.

As described above, according to the process for manufacturing the polymer specimen according to the embodiment of the present invention, when the polymer sample solution is electrosprayed on the sample plate placed on the sample stage 210, the mask 200 is used as shown in FIGS. 4*b* to 4*c* so that only a portion having a small thickness variation of 30% or less can be selected as a specimen from the regions where the polymer sample is widely sprayed on the sample plate. In order to adjust the position of the mask 200, the movement in the z-axis direction of the mask holder 310 on which the mask 200 is mounted is controlled by the spacer 330 between the mask holder 310 and the linear motion rail 320, the movement in the x-axis direction of the mask holder 310 on which the mask 200 is mounted is controlled by the linear motion rail 320, and the mask 200 may be moved in the y-axis direction within the opening 310*a* of the mask holder 310. However, the method of adjusting the position of the mask as described above is an embodiment of the method for manufacturing a specimen using the mask of the present invention. The present invention is not limited to the above, and various modifications and changes are possible with respect to the method of adjusting the position of the mask.

In addition, the electrospray device 10 used in one embodiment of the present invention may further comprise a sample injection adjusting unit (not shown), and the sample injection adjusting unit may specifically comprises a pump 30*a* for adjusting the injection amount of the polymer sample supplied to the main nozzle 110 and a pump 30*b* for adjusting the injection amount of the solvent supplied to the auxiliary nozzle 120. In addition, the amount of the sheath gas supplied to the sheath gas supply pipe 130 may be adjusted by a sheath gas adjusting unit (not shown).

As described above, according to the present invention, polymer specimens having a uniform thickness of 30% or less, such as 25% or less, obtained by electrospray through a mask can be prepared. The polymer specimen thus prepared can be applied to commercial MALDI-TOF MS equipment to obtain a reproducible MALDI spectrum with an error of ±30% or less, for example, ±15% or less, thereby enabling quantitative analysis of the polymer sample.

<Obtainment of MALDI Mass Spectrum>

The MALDI mass spectrum is obtained by irradiating a laser to each of the plurality of polymer specimens having a small thickness variation, and the signal intensity ratio of the polymer sample to the matrix or the signal intensity ratio of the polymer sample to the internal standard are calculated from the peak results of the spectrum.

The laser is a means for applying energy to the polymer specimen, and in particular, it may be a nitrogen laser or Nd:YAG laser.

When irradiating the laser to the specimen, a plurality of ion spectra may be obtained by irradiating to a single spot of the specimen many times, or irradiating to a plurality of spots of the specimen. For example, in order to obtain a spectrum having a good S/N ratio (signal-to-noise ratio), the MALDI mass spectrum may be obtained for several spots, for example, 20 to 80 spots at 50 to 2000 shots per spot of the specimen and thereafter an average value may be determined. In addition, experiments may be performed 3 times or more on specimens with the same conditions.

According to an embodiment of the present invention, a data acquisition process using Imaging S/W (e.g., Fleximaging, Bruker Daltonics, Germany) may be performed to obtain a MALDI mass spectrum.

FIG. 6 shows a data acquisition process from the MALDI mass spectrum obtained for the specimen manufactured according to one embodiment of the invention. Referring to FIG. 6, a polymer specimen having a uniform thickness was produced by electrospray of the polymer sample through a mask, and spectrum data were collected using Imaging S/W for a plurality of spots in the same specimen, to determine an average value. It is found that a reproducible spectrum can be obtained at all spots.

Data of the MALDI mass spectrum obtained by the above process may have a value of RSD (relative standard deviation) indicating an error of ±30% or less. For example, a reproducible MALDI mass spectrum can be obtained in which an error may be ±15% or less when measured for three or more spots on the same specimen (spot-to-spot) and an error may be ±30% or less even when measured for three or more specimens manufactured under the same conditions (sample-to-sample).

The ions appearing in the MALDI mass spectrum are a protonated polymer sample, a protonated matrix, a protonated internal standard and fragment products occurred in the ion source. Therefore, the peak pattern of the MALDI mass spectrum is determined by the number of ion, signal ratio and the like.

<Preparation of Quantitative Calibration Curve>

In order to quantify the polymer using the MALDI mass spectrum obtained for the polymer specimen according to the present invention, a quantitative calibration curve may be prepared by plotting the signal intensity ratio calculated above.

For example, the quantitative calibration curve of the polymer specimen containing the polymer sample and the matrix may be prepared by plotting a signal intensity ratio of the polymer sample and the matrix from the MALDI mass spectrum obtained for the specimen according to the concentration of the polymer sample.

The quantitative calibration curve of the polymer specimen additionally containing the internal standard together with the polymer sample and the matrix may be prepared by calculating the signal intensity ratio of the polymer sample and the internal standard from the MALDI mass spectrum obtained for the specimen and plotting it according to the concentration ratio of the polymer sample and the internal standard.

All the calibration curves prepared according to one embodiment of the present invention appear linearity ($R^2 \geq 0.98$, see FIGS. 7 and 8).

In addition, the RSD (relative standard deviation) of each point in the calibration curve according to the present invention may be ±15% or less.

Hereinafter, embodiments of the present invention will be described in detail so that those skilled in the art can easily carry out the present invention. The present invention may, however, be embodied in many different forms and should not be construed as limited to the embodiments set forth herein.

Example 1

Step 1: Preparation of Polymer Specimen

A solution having Tinuvin® 622 (manufactured by BASF) dissolved in xylene as a polymer compound to be analyzed was prepared at each concentration of 0.1 mg/mL, 0.5 mg/mL, 1 mg/mL and 3 mg/mL. The said solution, a solution of DCTB (trans-2-[3-(4-tert-butylphenyl)-2-methyl-2-propenylidene]malononitrile) (10 mg/mL THF) as a matrix and a solution of NaTFA (sodium trifluoroacetate) (0.02 M in THF) were mixed in a volume ratio of 9:1:1 to prepare a polymer sample solution. At this time, the polymer compound solution was used for each concentration to prepare a plurality of polymer sample solutions.

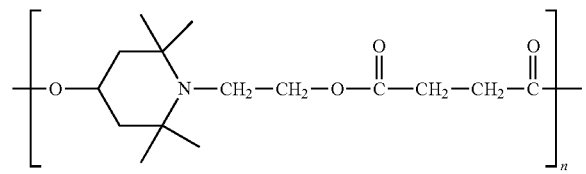

Tinuvin 622

The plurality of polymer sample solutions prepared above were electrosprayed using the electrospray apparatus 10 and the mask 200 having a hole with a diameter of 2 mm in FIG. 4c, respectively, to prepare a plurality of polymer specimens.

Specifically, the polymer sample was electrosprayed for 10 minutes at a flow rate of 0.5 μL/min ($1^{st}$ flow) on a stainless steel plate, and the thickness of the electrosprayed specimen was measured. However, the stainless steel plate has a rough surface such that it is not suitable to measure the thickness of the specimen. Therefore, in order to measure the thickness of the electrosprayed specimen, the polymer sample solution was again electrosprayed for 10 minutes at a flow rate of 0.5 μL/min ($1^{st}$ flow) on an ITO glass, and then the thickness of the specimen was measured at 2 μm intervals using an optical profiler. The average thickness for the measured thickness profiles was about 1 μm (see FIG. 5).

In addition, assuming that the spot size of the MALDI laser is 50 μm, the standard deviation of the average of the 25 measured values was measured, and as a result the thickness variation was about 25%.

Step 2: Obtainment of MALDI Mass Spectrum Using a MALDI-TOF mass spectrometer (UltrafleXtreme, Bruker Daltonics, Germany), MALDI mass spectrometry was performed by irradiating with 337 nm nitrogen laser (MNL100, Lasertechnik Berlin, Berlin, Germany) to 20 spots at 2000 shots per spot for each polymer specimen manufactured in the step 1.

Such mass spectrometry was performed in triplicate for each polymer specimen (i.e., for each concentration of polymer sample) to obtain a MALDI mass spectrum.

Subsequently, signal intensity ratios were calculated and averaged using the signals of Tinuvin® 622 as a polymer and the signals of the DCTB dimer peak and DCTB trimer peak as a matrix.

Step 3: Preparation of Quantitative Calibration Curve

A calibration curve was prepared by plotting signal intensity ratios of the Tinuvin® 622 and DCTB dimer peak or DCTB trimer peak calculated in the step 2 according to the concentration of Tinuvin® 622, and the results are shown in FIG. 7.

As can be seen from FIG. 7, using the signals of Tinuvin® 622 and the signals of the DCTB dimer peak (FIG. 7A) and DCTB trimer peak as a matrix (FIG. 7B) from the spectra obtained by performing MALDI on the uniform polymer specimen with a small thickness variation of 25%, a linear calibration curve ($R^2=0.08$ or more) having RSD (relative standard deviation) of each point within 15% was obtained.

Example 2

Step 1: Preparation of Polymer Specimen

A solution having BHB-PPG dissolved in THF (tetrahydrofuran) as a polymer compound to be analyzed was prepared at each concentration of 0.1 mg/mL, 1 mg/mL, 2 mg/mL, 5 mg/mL and 10 mg/mL. A solution having PPG dissolved in THF (0.5 mg/mL) as an internal standard, a solution having DCTB (trans-2-[3-(4-tert-butylphenyl)-2-methyl-2-propenylidene]malononitrile) dissolved in THF (10 mg/mL) as a matrix and a solution of NaTFA (0.02 M in THF) were prepared.

The matrix solution, the NaTFA solution, the polymer solution, and the internal standard solution were mixed in 9/1/0.5/0.5 (v/v/v/v). At this time, the polymer compound solution was used for each concentration to prepare a plurality of polymer sample solutions.

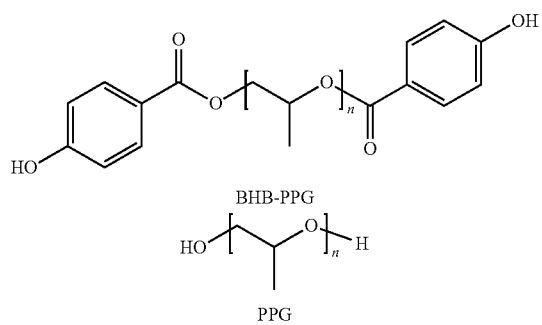

BHB-PPG

PPG

The plurality of polymer sample solutions prepared above were electrosprayed using the electrospray apparatus 10 and the mask 200 having a hole with a diameter of 2 mm in FIG. 4c, respectively, to prepare a plurality of polymer specimens.

Specifically, the polymer sample was electrosprayed for 10 minutes at a flow rate of 0.5 μL/min (1st flow) on a stainless steel plate, and the thickness of the electrosprayed specimen was measured. However, the stainless steel plate has a rough surface such that it is not suitable to measure the thickness of the specimen. Therefore, in order to measure the thickness of the electrosprayed specimen, the polymer sample solution was again electrosprayed for 10 minutes at a flow rate of 0.5 μL/min (1st flow) on an ITO glass, and then the thickness of the specimen was measured at 2 μm intervals using an optical profiler. The average thickness for the measured thickness profiles was about 1 μm. Assuming that the spot size of the MALDI laser is 50 μm, the standard deviation of the average of the 25 measured values was measured, and as a result the thickness variation was about 25%.

Step 2: Obtainment of MALDI Mass Spectrum

Using a MALDI-TOF mass spectrometer (UltrafleXtreme, Bruker Daltonics, Germany), MALDI mass spectrometry was performed by irradiating with 337 nm nitrogen laser (MNL100, Lasertechnik Berlin, Berlin, Germany) to 40 spots at 50 shots per spot (total 2000 shots) for each polymer specimen manufactured in the step 1. Imaging S/W (Fleximaging, Bruker Daltonics, Germany) was used to collect the MALDI spectrum (see FIG. 6).

Such mass spectrometry was performed in triplicate for each polymer specimen (i.e., for each concentration of polymer sample) to obtain a MALDI mass spectrum. Subsequently, signal intensity ratios of the polymer sample (BHB-PPG) and the internal standard (PPG) were calculated and averaged.

Step 3: Preparation of Quantitative Calibration Curve

A calibration curve was prepared by plotting signal intensity ratios of BHB-PPG and PPG calculated in the step 2 according to the concentration ratio of BHB-PPG to PPG, and the results are shown in FIGS. 8a to 8c.

FIGS. 8a to 8c are linear calibration curves prepared using polymer peaks having the number of repeating unit of the monomer of n=27, n=33 and n=38 in MALDI mass spectra obtained for each concentration of BHB-PPG/PPG. It is found that a linear calibration curve can be obtained for any of polymer peaks having any number of repeating units. In addition, it is found that RSD (relative standard deviation) of the average value of the MALDI spectrum for BHB-PPG/PPG is within 13%, which means that reproducibility is very high.

Comparative Example 1

Using the polymer sample solution prepared in the step 1 of Example 2, two specimens were prepared by a dried droplet method, and MALDI mass spectrometry was performed at 6 spots for each of the prepared specimens.

FIG. 9 shows a result of the reproducibility evaluation of the MALDI mass spectrum for the specimens prepared in Example 2 and Comparative Example 1. It is found that the reproducibility of the spectrum is higher for the specimen of Example 2 prepared using the electrospray and the mask.

What is claimed is:

1. A method for relative quantitative analysis of a polymer by MALDI mass spectrometry, comprising the steps of:
    (S1) preparing a plurality of polymer specimens having a thickness variation of 30% or less by electrospray of a solution containing a polymer sample and a matrix through a mask for each concentration of the polymer sample;
    (S2) obtaining a MALDI mass spectrum by irradiating a laser to each of the plurality of polymer specimens; and
    (S3) preparing a quantitative calibration curve with a signal of the polymer sample from peak results of the MALDI mass spectrum.

2. The method for relative quantitative analysis of a polymer according to claim 1, wherein the polymer sample comprises poly-(N-β-hydroxyethyl-2,2,6,6-tetramethyl-4-hydroxypiperidylsuccinate (Tinuvin 622), 2,2-bis(hydroxymethyl)butyric acid-poly(propylene glycol) (BHB-PPG), allylphenol-polydimethylsiloxane (AP-PDMS), H-polydimethylsiloxane (H-PDMS) or mixtures thereof.

3. The method for relative quantitative analysis of a polymer according to claim 1, wherein the quantitative calibration curve is prepared by calculating a signal intensity ratio of the polymer sample and the matrix from the peak results of the MALDI mass spectrum and plotting it according to the concentration of the polymer sample.

4. The method for relative quantitative analysis of a polymer according to claim 1, wherein in the step (S1), each of the polymer specimens is prepared by additionally adding an internal standard to the solution containing the polymer sample and the matrix.

5. The method for relative quantitative analysis of a polymer according to claim 4, wherein the quantitative calibration curve for the polymer specimen having the polymer sample and the matrix additionally added with the internal standard is prepared by calculating a signal intensity ratio of the polymer sample and the internal standard from the MALDI mass spectrum obtained for the polymer specimen, and plotting it according to the concentration ratio of the polymer sample and the internal standard.

6. The method for relative quantitative analysis of a polymer according to claim 4, wherein the internal standard is a polymer compound selected from poly(ethylene glycol) (PEG), poly(propylene glycol) (PPG), polystyrene (PS), or mixtures of two or more thereof.

7. The method for relative quantitative analysis of a polymer according to claim 1, wherein the preparing each of the polymer specimens by electrospray through the mask comprises the steps of:
    (i) preparing an electrospray apparatus comprising a sample plate and an electrospray main nozzle and mounting the mask on the sample plate; and
    (ii) electrospraying the solution containing the polymer sample and the matrix onto the mask-mounted sample plate by the main nozzle,
    wherein the mask comprises a hole through which the polymer sample solution electrosprayed from the main nozzle passes onto the sample plate so as to obtain a polymer specimen having a small thickness variation on the sample plate.

8. The method for relative quantitative analysis of a polymer according to claim 7, wherein in the step (ii), the electrospray is performed after additionally adding an internal standard to the solution containing the polymer sample and the matrix.

9. The method for relative quantitative analysis of a polymer according to claim 7, wherein the hole in the mask has a diameter of 1 to 2 mm.

10. The method for relative quantitative analysis of a polymer according to claim 7, wherein the mask is made of stainless steel or aluminum.

11. The method for relative quantitative analysis of a polymer according to claim 7, wherein the mounting of the mask on the sample plate further comprises the step of adjusting position of the mask in a direction of at least one of the x-axis, the y-axis or the z-axis.

12. The method for relative quantitative analysis of a polymer according to claim 7, wherein the electrospray apparatus further comprises an auxiliary nozzle surrounding the main nozzle and coaxial with the main nozzle, and the electrospraying the polymer sample solution onto the sample plate by the main nozzle further comprises the step of spraying a solvent by the auxiliary nozzle to prevent the matrix from being deposited around the main nozzle.

13. The method for relative quantitative analysis of a polymer according to claim 12, wherein the electrospray apparatus further comprises a sheath gas supply pipe surrounding the auxiliary nozzle and coaxial with the auxiliary nozzle, and the electrospraying the polymer sample solution onto the sample plate by the main nozzle further comprises the step of spraying a sheath gas from the sheath gas supply pipe to guide the solution so that the solution is sprayed to a predetermined position of the sample plate.

14. The method for relative quantitative analysis of a polymer according to claim 7, wherein the area where the polymer sample solution is electrosprayed on the sample plate is 40 to 180 $mm^2$.

15. The method for relative quantitative analysis of a polymer according to claim 14, wherein the area where the polymer sample solution is electrosprayed on the sample plate is 40 to 80 $mm^2$.

16. The method for relative quantitative analysis of a polymer according to claim 1, wherein each of the polymer specimens has a thickness in the range of 500 nm to 10 μm.

17. The method for relative quantitative analysis of a polymer according to claim 1, wherein the thickness variation of the polymer specimen is measured at three or more spots on the same one of the polymer specimens (spot-to-spot).

18. The method for relative quantitative analysis of a polymer according to claim 1, wherein a relative standard deviation (RSD) range, which indicates an error of a result of the MALDI mass spectrum measured on each of the polymer specimens, is ±15% or less as measured at three or more spots on the same one of the polymer specimens (spot-to-spot).

19. The method for relative quantitative analysis of a polymer according to claim 1, wherein the quantitative calibration curve is linear.

\* \* \* \* \*